United States Patent [19]

Chen et al.

[11] Patent Number: 4,876,380

[45] Date of Patent: Oct. 24, 1989

[54] COLOR REDUCTION OF POLYMERIC ISOCYANATES VIA MULTIPLE SOLVENT FRACTIONATION

[75] Inventors: Lao-Jer Chen; Steven B. Lowenkron, both of Houston, Tex.

[73] Assignee: The Dow Chemical Company, Midland, Mich.

[21] Appl. No.: 239,082

[22] Filed: Aug. 31, 1988

[51] Int. Cl.$^4$ .............................................. C07C 143/00
[52] U.S. Cl. ..................................................... 560/352
[58] Field of Search ......................................... 560/352

[56] References Cited

U.S. PATENT DOCUMENTS 3,211,631 10/1965 Fuchs .
3,479,384 11/1969 Heiss .
3,892,634 7/1975 Hajek et al. .
3,912,600 10/1975 Hatfield et al. .
4,189,354 2/1980 Ellendt et al. .
4,193,932 3/1980 Yamamoto et al. .

Primary Examiner—Alan Siegel
Attorney, Agent, or Firm—James S. Rose

[57] ABSTRACT

Disclosed is an extraction process wherein a crude polyisocyanate is separated into a purified fraction and residual fraction wherein the purified fraction is characterized by greatly improved color over the crude material but with little or no difference in viscosity. The residual fraction remains perfectly useful for those applications where color is not a critical requirement.

Significantly, the disclosed purification is achieved with literally a 100 percent material balance. No loss in polyisocyanate is encountered.

16 Claims, 1 Drawing Sheet

COLOR REDUCTION OF POLYMERIC ISOCYANATES VIA MULTIPLE SOLVENT FRACTIONATION

FIELD OF THE INVENTION

This invention relates to the purification of organic polyisocyanates and, more particularly, is concerned with a solvent extraction method for providing a purified fraction of a polyisocyanate from a crude mixture.

DESCRIPTION OF THE PRIOR ART

The purification of crude organic polyisocyanates, short of actual distillation, has long been recognized as a difficult and tedious operation. Even distillation procedures are not without problems because the majority of polyisocyanates are sensitive to elevated temperatures forming polymers and tars. In a number of cases, one is dealing with crude polyisocyanates which, for one reason or another, cannot be distilled without causing much product loss. Amongst the problems encountered is the propensity for side-product formation during their preparation which becomes even more acute when the polyisocyanates are derived from the phosgenation of the precursor polyamines in organic solvents. Further, complications arise when the polyisocyanate is in the form of a crude oligomeric mixture to begin with which prevents the distillation of anything but the lower functionality diisocyanate component. Typical of such mixtures are the well-known polymethylene poly(phenyl isocyanate) mixtures (hereinafter PMDI) obtained from the phosgenation of the corresponding polymethylene poly(phenylamine) mixtures which in turn are prepared by the also well-known acid catalyzed aniline/formaldehyde condensation reaction.

Generally speaking, the methods for purifying such crude mixtures begin with the final isocyanate products, primarily because it is during the phosgenation reaction where most of the troublesome impurities are formed. Foremost of the purification methods are those employing at least one distillation step. However, as previously noted, distillation for the whole mixture is not possible when oligomeric mixtures are involved unless only a diisocyanate is produced. Additionally, distillation procedures invariably lead to high product losses unless one chooses to effect the distillation following certain procedures. U.S. Pat. No. 3,892,634 discloses a distillation method for obtaining pure methylenebis(phenyl isocyanate) while providing a relatively pure PMDI residue. U.S. Pat. No. 4,189,354 discloses a similar type distillation of PMDI except for the additional distillation step wherein up to 10 weight percent of the feed material is run off as a sump. Another known purification method is where a portion of the solvent from a solution of the crude PMDI is flashed off under pressure as taught in U.S. Pat. No. 3,912,600. This results in a polyisocyanate having reduced acidity and hydrolyzable chloride levels. Yet another technique is described in U.S. Pat. No. 4,193,932 wherein hydrogen chloride gas is passed through a solution of the isocyanate.

A solvent extractive method is disclosed in U.S. Pat. No. 3,211,631 which recovers the toluene diisocyanate product remaining mixed in the still bottoms after the main fraction of diisocyanate has been removed by distillation. The method simply involves the extraction of the diisocyanate from the residue by the solvent which results in the solvent layer with the product and the second layer of insoluble tars. U.S. Pat. No. 3,479,384 discloses the extraction of a crude polyisocyanate with a solvent pair. One is capable of dissolving all the crude material while the second is a non-solvent only for the higher molecular weight polymeric products and reaction by-products in the crude material. While this extraction process does provide the polyisocyanate product with much improved color, that is to say, a light yellow when measured on the Yellow Index scale (discussed below), it always leads to a dramatic reduction in the viscosity of the polyisocyanate.

In some applications, the reduction in polyisocyanate viscosity can be tolerated so long as the isocyanate color is reduced. However, in the polyurethane art a body of machine mixing technology has been developed over the years. Around this technology, many of the processing mixers and pumps have been designed to operate most effectively. In this connection, much of the technology is designed for an A side polyisocyanate component viscosity somewhere in the range of about 125 to about 750 cps (measured at 25° C.). Below the 100 cps level problems in matching pumping ratios of an A side with a much higher viscosity B side polyol can occur. Accordingly, the method disclosed in the '384 patent tends to exclude a substantial portion of the purified isocyanate from these machine processes.

There still remains a need for a purified organic polyisocyanate, particularly a polymethylene poly(phenyl isocyanate), which has not suffered a viscosity loss to any degree when purified for color removal.

SUMMARY OF THE INVENTION

The present invention is directed to a process for extracting a crude organic polyisocyanate obtained from the phosgenation of a precursor organic polyamine to form a purified fraction and a residual fraction said process comprising:

1. extracting said crude polyisocyanate in a first extractor with a solvent pair comprising at least one first solvent capable of solubilizing substantially all of said crude polyisocyanate and at least one second solvent capable of solubilizing all but the high boiling higher polymeric components present in said crude polyisocyanate thereby forming a first top layer comprising said second solvent and a first bottom layer comprising said first solvent;

2. passing said first bottom layer, optionally through an evaporator, to a second extractor;

3. extracting said first bottom layer in said second extractor with said solvent pair set forth above thereby forming a second top and second bottom layers;

4. passing said second top layer through an evaporator to recover said second solvent as overhead and said purified fraction as residue; and 5. passing said second bottom layer, optionally through an evaporator, and in combination with said first top layer to an evaporator to recover said second solvent, and, optionally, said first solvent as overhead and said residual fraction as residue.

Surprisingly, by the simple expedient of carrying out a double extraction in the manner set forth above a purified fraction of a polyisocyanate is obtained meeting the requirements set forth above for a combination of both improved color over the crude polyisocyanate with a viscosity, if not within the same range as the crude material, at least close enough to be compatible with a majority of existing polyurethane mixing and dosing equipment. It will be recognized that this present method of solvent extraction differs from the well-known multiple extractions where like-solvent fractions only are combined. The present method involves the combination of unlike-solvent fractions.

The residual fraction, while probably having somewhat darker color than the starting crude material, is still useful for all those applications calling for polyisocyanates where color is not of primary concern.

Furthermore, in an additional and unexpected benefit to flow from the present process, the acid impurities and iron contaminants are reduced considerably in the purified fraction over the starting isocyanate.

DETAILED DESCRIPTION OF THE INVENTION

Figure 1:
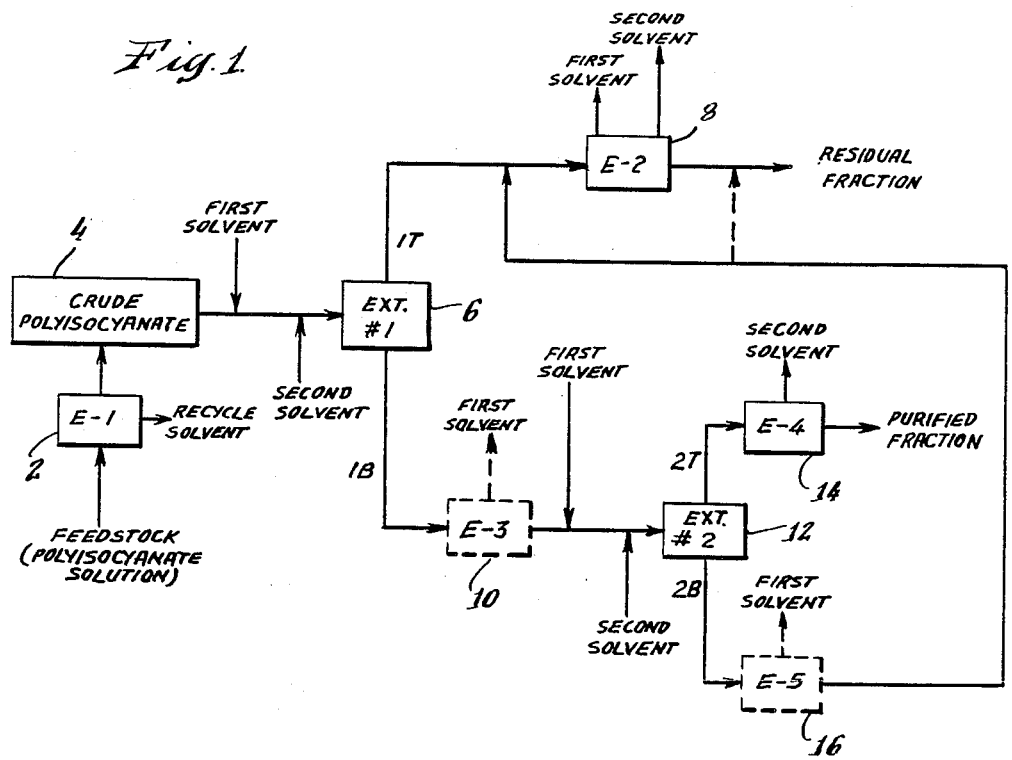
FIG. 1 shows a flow sheet illustrating in schematic form the process according to the invention.

The present process is readily adaptable to the purification of any crude organic polyisocyanate whether it be distillable in whole, in part, or not at all. If color bodies are present along with, or, because of, impurities arising from higher polymeric components, high boiling impurities, and the like, then purification of the crude material can be effected by the present method. Generally speaking, such impurities are associated with the production of polyisocyanates by the phosgenation of precursor organic polyamines by well-known phosgenation methods. Discussions of some of these impurities and means for their reduction in crude polyisocyanates such as PMDI mixtures and crude toluene diisocyanate mixtures are set forth in typical U.S. Pat. Nos. 3,912,600, 4,189,354, and 4,193,932. It is those crude organic polyisocyanates obtained via this phosgenation route which are most amenable to purification by the present method, and, accordingly, benefit most by the method.

Typical, and preferred, crude polyisocyanates for purification by this method are the crude PMDI mixtures obtained from the phosgenation of polymethylene poly(phenylamines). The latter polyamines are obtained from well-known acid catalyzed aniline/formaldehyde condensation reaction. The preparation of such crude polyisocyanate mixtures is illustratively disclosed in U.S. Pat. Nos. 3,857,871 and 3,912,600 whose disclosures relative thereto are incorporated herein by reference. Generally speaking, the mixtures contain from about 20 to about 85 percent by weight methylenebis(-phenyl isocyanate) and the remainder being polymethylene poly(phenyl isocyanates) of functionality higher than 2. Included in such mixtures are any of the isomeric isocyanates which generally are high in the 4,4'- but can include up to 30 or more percent 2,4'-, and trace amounts of the 2,2'-methylenebis(phenyl isocyanate).

In one embodiment the crude PMDI is obtained directly from a feedstock coming from the phosgenation of the polyamine after the phosgene has been removed. In an optional embodiment the solvent is stripped from the crude isocyanate prior to the first extraction step. In another embodiment the solvent is partially stripped to provide a solution of the PMDI dissolved in the same or different solvent employed in said first extraction. This will be discussed in more detail below.

The actual extraction steps can be carried out in a static or continuous manner using conventional small scale laboratory apparatus or plant scale continuous liquid-liquid extraction equipment. The novel aspect of the process resides in the combination of extraction steps in conjunction with how the extracts are combined.

The first extracting step is carried out with a solvent pair defined above as a first and second solvent wherein the first is capable of solubilizing or easily dissolving substantially all of the crude organic polyisocyanate, whereas the second is capable of solubilizing or easily dissolving the major portion of the polyisocyanate but has poor affinity or dissolving power for high molecular weight impurities and color bodies. An object of this first step is the formation of a top layer comprising the second solvent with the bottom layer comprising the first.

Any suitable organic solvent which is free of groups or impurities reactive with isocyanate may be used. Single solvents or mixtures thereof which will act to dissolve substantially all of the crude polyisocyanate can be employed as the first solvent. Single solvents or mixtures thereof which will act to dissolve all but the high boiling higher polymeric or oligomeric impurities and color bodies in the crude polyisocyanate can be employed as the second solvent. Generally speaking, it is preferable to choose both solvents which will have boiling points within a range of from about 20° C. to about 200° C., preferably from about 40° C. to about 185° C. This permits ease of handling of the extraction mixtures particularly separation of the solvents from isocyanate by distillation processes. It is also desirable to choose a solvent pair such that their densities differ sufficiently to facilitate easy separation. This is particularly important if continuous extraction steps are contemplated. Generally speaking, the choice of first solvents is considerably larger than for second solvent.

Illustrative of the first solvents are aromatic hydrocarbons such as benzene, toluene, xylene, diethylbenzene, isobutylbenzene, and the like; halogenated aromatic hydrocarbons such as chlorobenzene, ortho-dichlorobenzene, bromobenzene, and the like; halogenated aliphatic hydrocarbons such as 1,1,1,3-tetrachlorotetrafluoropropane, 1,1,1-trichloropentafluoropropane, 1,1,1-dichlorofluoro-2,2,2-chlorodifluoroethane, dibromotetrafluoroethane, 1,1,1-dichlorofluoro-2,2,2-dichlorofluoroethane, carbon tetrachloride, trichloroethylene, chloroform, methylene dichloride, ethylene dichloride, ethylene bromide, perchloroethylene, and the like; petroleum solvent mixtures containing both alkyl and aromatic hydrocarbons, and the like; esters such as ethyl acetate, propyl acetate, butyl acetate, amyl acetate, ethyl butyrate, and the like; ketones such as acetone, methyl ethyl ketone, diisobutyl ketone, methyl isobutyl ketone, and the like; and mixtures of any of the above in any proportions.

A preferred group of first solvents comprises toluene, xylene, monochlorobenzene, o-dichlorobenzene, methylene dichloride, and mixtures thereof. A particularly preferred solvent is methylene dichloride.

Illustrative of the second solvents are aliphatic hydrocarbons having from 5 to 10 carbon atoms such as pentane, hexane, heptane, octane, nonane, decane, and isomeric forms thereof, and the like; alkenes having from 5 to 10 carbon atoms such as 1-pentene, 1-hexene, 1-heptene, 1-octene, 1-nonene, 1-decene, and isomers thereof including double bond positional isomers, and carbon-carbon positional isomers, and the like; petroleum ethers, light napthas or ligroin, and the like.

A preferred group of second solvents is comprised of the aliphatic hydrocarbons having from 5 to 10 carbon atoms. A particularly preferred group consists of pentane and hexane.

The order in which the crude polyisocyanate is mixed with the solvent pair is not in any way critical. The crude isocyanate can be added to the first solvent or vice versa to be followed by the second solvent and whatever means for agitation then applied. This is followed by separating the layers and following the procedure described above. Alternatively, the second solvent can be reversed with the first initially. Generally speaking, it is found most convenient to dissolve the polyisocyanate in the first solvent initially. Not only is this mode most convenient for a static extraction process, but lends itself directly into a continuous process, particularly where the feedstock to the first extraction is derived directly from a phosgenation process.

In respect of the first and second solvent proportions to be employed, much will depend on the levels of impurities including color bodies and the viscosities of the crude polyisocyanates. In fact, the magnitude of the latter property will govern its magnitude in both the purified product and the residue. Suffice it to say that the optimum proportions to be employed in the extraction are easily determined by simple trial and error experiments on aliquot samples. The chosen proportions should result in a color improvement in the final purified fraction of at least about 35 percent, and, preferably at least about 60 percent as measured by Yellow Index color in accordance with modified ASTM Test Method D 1925-70 described below. Concomitantly, the proportions should be such that the purified fraction will have a viscosity falling within a range of from about 125 to about 750 cps (at 25° C.), preferably from about 165 to about 225 cps. However, it should be recognized that these viscosity ranges will be governed largely by the viscosity of the starting crude material so that an expression of preference for this property is, at the same time, an expression of preference for the starting viscosity. By way of explanation, one of the most unexpected observations in the present method is the fact that the viscosities of the purified fractions remain essentially within the same range as the crude material but have greatly improved color by Yellow Index measurement. However, this is not to say that the present process cannot be used with crude polyisocyanates having lower viscosities. In fact, this method can be employed with lower viscosity materials of which toluene diisocyanate is a prime example.

Another gauge by which the optimum solvent proportions can be selected lies in the resulting distribution of isocyanate in the first and second solvent. It has been observed generally that optimum results regarding ultimate polyisocyanate purity are achieved when in the first extraction the distribution of polyisocyanate material is from about 45 to about 55 percent by weight in the first solvent and the complementary 55 to 45 percent in the second solvent based on the input weight of the polyisocyanate.

Advantageously, the proportions of components in the first extraction step based on 100 volume percent are from about 5 to about 20 volume percent polyisocyanate, from about 10 to about 35 volume percent first solvent and from about 55 to about 85 volume percent second solvent. Preferably, these volume percent proportions fall within the respective ranges of from about 8 to 15, from about 10 to 30, and from about 60 to 80. A most preferred combination is about 10 volume percent polyisocyanate, about 12 to 30 percent first solvent, and about 60 to 80 second solvent.

After the first and second solvent fractions have separated into bottom and top layers respectively, their separation can be effected by any convenient means. The bottom layer can be handled in a number of ways. The solvent may be partially or completely removed using any conventional means such as distillation or flash distillation under reduced or atmospheric pressure prior to subjecting the polyisocyanate component to a second extraction step. Alternatively, and, preferably, the bottom layer with its solvent is subjected directly to the second extraction. This preferred embodiment lends itself most readily to a continuous operation.

The bottom layer either in neat form or else dissolved in residual first solvent is extracted with a first and second solvent in the same, or different extraction apparatus as the first depending primarily on whether the process is static or continuous. The same considerations discussed in detail above for the first extraction apply with equal force to this second extraction. That is to say, the order of mixing, the first and second solvent identities and preferences, the desired color improvements and viscosities of the final purified fraction, volume proportions of in-put polyisocyanate and solvents, and product distribution in the top and bottom layers, all are identically applied to this second extraction. If the first bottom layer is charged to the second extractor as a solution, then the volume percent of polyisocyanate is calculated on the basis of its actual content in the solution and the first bottom layer is employed in sufficient proportions to satisfy the 5 to 20 volume percent (or preferred ranges) for polyisocyanate content set forth above.

Similarly to the first extraction, optimum results are obtained when the in-put polyisocyanate is distributed in the first solvent (bottom layer) and second solvent (top layer) in from about 45 to about 55 weight percent and 55 to 45 percent, respectively.

The top layer is separated and passed to an appropriate distillation apparatus to remove the second solvent and leave the residue of purified fraction. The second solvent can be simply collected to be used again in a static process, or, alternatively, can be continuously recycled back to the first or second extractor where the process is on-going.

Meanwhile, the polyisocyanate in the bottom layer from this second extraction is ultimately combined with the polyisocyanate component in the top layer from the first extraction. How this is achieved is immaterial but the final combination comprises approximately 75 percent by weight of the original crude polyisocyanate if the 50/50 distribution is followed in both extractions. The second extraction bottom layer solution can be distilled prior to its combination with the first top layer. Preferably, it is combined directly with the first top layer solution and first and second solvent is removed using conventional distilling methods to provide the residual fraction. The solvents can be employed in further static steps or else they can be continuously cycled to the first or second extractors.

In order to facilitate further an understanding of the invention reference is made to FIG. 1 which shows in schematic form one embodiment of the process. A supply of crude polyisocyanate is shown at (4) entering the first extractor (6) along with the first and second solvents. The crude polyisocyanate can be either neat or else already dissolved in a first solvent which latter can be the same as, or, different from, the first solvent being fed to (6). If solvent is originally present, then it can form either the total amount of first solvent required or else serve only as a portion which must be augmented by adding first solvent. FIG. 1 actually shows the source of this polyisocyanate supply as the feedstock coming from the phosgenation of a precursor polyamine after the phosgene has been stripped and solvent either partially or completely removed in an evaporator at E-1 (2). The evaporator represents any type of apparatus capable of removing solvent from the feedstock and condensing the overhead in a heat exchanger or condenser to obtain recycle solvent for further use. Solvent removal at this stage can be total or partial whichever is desired. This particular type of supply of crude polyisocyanate lends itself to a continuous operation if desired.

Accordingly, the crude polyisocyanate is extracted at (6) with the first and second solvents according to the teaching set forth above. The extractor can range from a simple laboratory scale separatory funnel to any of the large scale liquid-liquid extractors. Typical of such units are spray columns wherein one phase is pumped through a spray nozzle and dispersed into small droplets which then move through the other phase due to density difference; baffle columns, packed columns, plate columns all designed to increase surface contact between phases; mixer-settler columns; internally agitated columns, and any other of the conventionally employed extraction equipment known to those skilled in the art.

The bottom layer designated (1B) from the first extractor is then transferred, optionally through an evaporator E-3 (10) to remove first solvent, to the second extractor (12) for the second extraction step with first and second solvents. Preferably, the solvent in (1B) serves as part of the first solvent needed in the second extractor. As noted previously, the volume percent of polyisocyanate in this second extraction is based on the actual volume percent available from (1B). The second extractor apparatus can be of the same or different type as the first. Ordinarily, they are of the same type. In fact, in a static process in accordance with this invention, both steps can be carried out in the same extractor but in a continuous process they must be different.

The top layer from (12) designated (2T) is passed through an evaporator E-4 (14) to remove second solvent as overhead to storage or else back to first or second extractors. The residue from this step is the purified fraction of the polyisocyanate.

The bottom layer from (12) designated (2B), is optionally passed through an evaporator E-5 (16) to recover first solvent, or, directly combined with the top layer from the first extraction, namely (1T), to pass through the evaporator E-2 (8) to recover both first and second solvents for storage or recycle. The residue from this evaporator step is the residual fraction.

Figure 2:
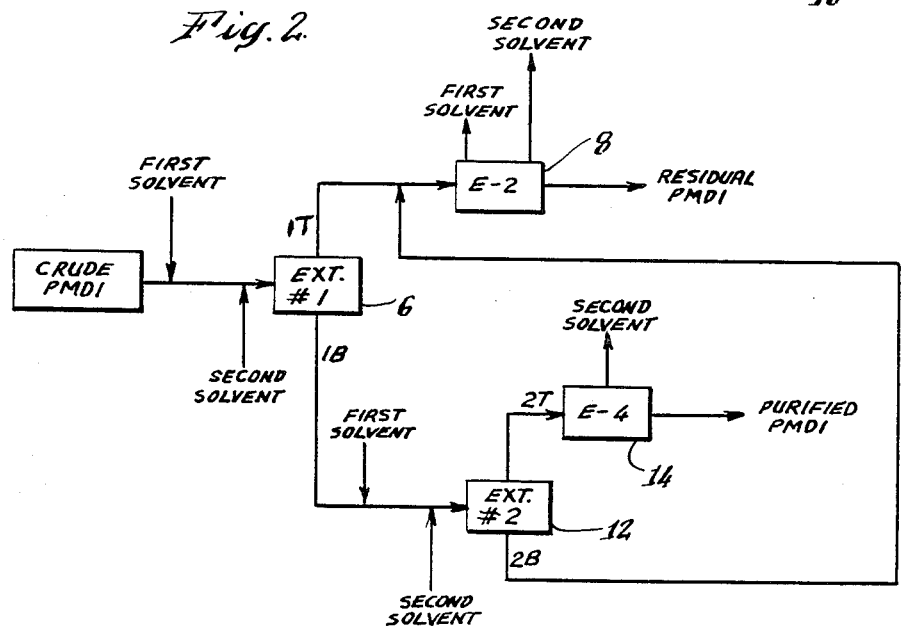
FIG. 2 shows a flow sheet of one preferred embodiment of a process according to the invention.

One of the preferred embodiments of the present process is shown schematically in FIG. 2 wherein the crude polyisocyanate is a PMDI discussed above and is shown entering the first extractor (6) as PMDI. Generally speaking, this polyisocyanate is prepared in chlorobenzene which can serve as part or all of the first solvent called for in the extraction either in a static or continuous process. In FIG. 2 the PMDI is shown without solvent entering the first extractor where the layers resulting therefrom are separated into the (1T) and (1B) layers. The (1B) bottom layer with its solvent is passed directly to the second extractor (12) where additional first solvent along with the second solvent are added to perform the second extraction. The top layer (2T) is evaporated at E-4 (14) to provide second solvent overhead and the purified PMDI as residue. The bottom layer (2B) is combined with (1T) from the first extraction and both first and second solvents removed at E-2 (8) to provide the residual PMDI.

A distinct benefit of the present invention is the fact that a highly purified fraction of polyisocyanate is obtained without any overall loss in material balance. That is to say, of the crude polyisocyante put into the process, the recovery is essentially 100 percent between the purified fraction and the residual polyisocyanate. For the most part, the recovery is approximately 25 percent by weight in the purified fraction and the balance of 75 percent in the residue when the 50/50 weight percent distribution is followed in both extractions. The process is not necessarily limited only to this distribution but some of the most beneficial effects are observed when these ratios are observed.

The purified fraction of polyisocyanate, particularly in reference to PMDI will have the viscosity range falling within the values of from about 125 to about 750 cps, and preferably within the range of about 165 to about 225 cps with its color improved by at least 25 percent and preferably by at least 60 percent as discussed fully above.

The surprising feature is the fact that this color improvement is effected with virtually no lowering of the viscosity from the starting crude polyisocyanate level so that the improved product can be plugged directly into known polyurethane and/or polyisocyanurate machine formulations.

Additionally, the purified fractions have distinctly lowered acidity and hydrolyzable chloride levels over the crude material and virtually complete elimination of iron.

Generally speaking, the present process results in transferring the impurities from the purified fraction to the residual fraction resulting in higher color, and acid impurities in the latter. However, the residual fraction is entirely useful, in those applications in polyurethane manufacture in particular wherein acid impurities, and color are not critical. A perfect example is the manufacture of polyurethane laminates wherein the polymer is being formed between various types of facer materials.

Accordingly, the present process provies approximately 25 percent by weight of purified polyisocyanate for critical applications and approximately 75 percent for those applications wherein color and purity are not critical.

The following examples describe the manner and process of making and using the invention and set forth the best mode contemplated by the inventors of carrying out the invention but are not to be construed as limiting.

EXAMPLE 1

The following experiment describes the extraction of a crude polymethylene poly(phenyl isocyanate) into a purified fraction designated second top (2T) and a residual fraction designated combined first top plus second bottom (1T2B) in accordance with the present invention.

A 2-liter narrow mouth reagent bottle is charged with 237.4 g (190 ml) of a polymethylene poly(phenyl isocyanate) mixture comprised of about 44 percent by weight methylenebis(phenyl isocyanate) with the remainder being polymethylene poly(phenyl isocyanates) of functionality greater than 2.0. The properties of this material are set forth in Table I below in the column marked Control. Added to the bottle are 247 ml of methylene dichloride and 1463 ml of pentane. The mixture is thoroughly shaken manually for about 2 to 3 minutes at ambient temperature (about 20° C.) then allowed to stand for about three hours. At the end of this period the mixture settles into two distinct layers, i.e. a light colored top layer of pentane solution designated (1T) and a darker colored bottom layer of methylene dichloride solution designated (1B).

The top layer is separated from the bottom layer by inserting a dip tube below the surface of the upper layer and applying a nitrogen pressure of about 5 pounds pressure. The bottom layer (1B) comprises about 93.4 ml of polymethylene poly(phenyl isocyanates) in solution with about 40 ml of methylene dichloride. This bottom layer is subjected to an extraction when 236.8 ml of methylene dichloride and 584.2 ml of pentane are added to the reagent bottle, shaken, and allowed to settle as described above. The mixture settles into two distinct layers, i.e. a light colored top layer of pentane solution designated (2T) and darker colored bottom layer of methylene dichloride solution designated (2B).

The top layer (2T) is heated under vacuum (about 1 mm of mercury) at a temperature of about 50° C. in a rotary evaporator to remove all of the solvent leaving a purified fraction of 64.4 g polymethylene poly(phenyl isocyanates) having the properties set forth below. Similarly, the solvents were removed from the (1T) and (2B) layers to provide 123.4 g and 51.4 g, respectively, which are combined to provide the (1T2B) or residual fraction of polymethylene poly(phenyl isocyanates) having the properties set forth below.

TABLE I

| Sample | Control | 2T | 1T2B |
| --- | --- | --- | --- |
| Viscosity (cps) at 25° C. | 191 | 217 | 180 |
| Yellow Index[1] | 31.5 | 10.0 | 40 |
| Fe ppm | 6 | 1 | 9 |
| Isocyanate E.W. | 133.8 | 132.6 | 134.7 |
| % Hot HCl[2] | 0.04 | 0.03 | 0.05 |
| % Total Cl[2] | 0.27 | 0.18 | 0.29 |

Footnotes to Table I
[1]Yellow Index: yellow color index determined by modified ASTM Test Method D 1925-70 using a solution of 1% isocyanate in monochlorobenzene (w/v).
[2]% Hot HCl: Test procedure described in U.S. Pat. No. 3,793,362 (col. 7, line 24 to col. 8, line 12) and is the free acid generated upon subjecting a measured quantity of polyisocyanate to brief period of heating in methanol and determined by potassium hydroxide titration; % Total Cl also described in the '362 patent and is the hydrolyzable chloride determined by silver nitrate titration of the chloride ion generated by boiling a measured amount of polyisocyanate in a mixture of toluene and methanol.

The purified fraction (2T) has the viscosity level within the same desirable level as the control while the color is much improved at a Yellow Index of 10 as opposed to 31.5 for the Control. At the same time the acid properties are improved over the Control by showing much improved % Total Cl and the iron is noticeably lower. The residual fraction still retains the desirable viscosity level while showing higher color than the Control.

These results are in contrast to the simpler extraction procedure according to U.S. Pat. No. 3,479,384 wherein only the one extraction is employed and the first top pentane layer contains the purified fraction of polyisocyanate with much improved color over the control but with about a three-fold decrease in viscosity.

EXAMPLE 2

The following describes a similar extraction to that set forth in Example 1 wherein a similarly constituted crude polyisocyanate and same solvent pair are employed in the first extraction step to provide top (1T) and bottom (1B) layers using identical proportions to those set forth above in Example 1.

The (1B) layer is extracted with 229 ml of methylene chloride and 612 ml of pentane to provide a top (2T) and bottom (2B) layers. Removal of solvent from (2T) provides 64.5 g of purified fraction, while removal of solvents from the (1T) and (2B) layers and their combination provides 171.1 g of residue fraction. The properties of these fractional products are set forth below.

TABLE II

| Sample | Control | 2T | 1T2B |
| --- | --- | --- | --- |
| Viscosity (cps) at 25° C. | 181 | 150 | 182 |
| Yellow Index | 36.3 | 9.8 | 44.4 |
| Fe ppm | 4 | 0 | 6 |
| Isocyanate E.W. | 132.9 | 131.8 | 133.9 |
| % Hot HCl | 0.04 | 0.03 | 0.05 |
| % Total Cl | 0.30 | 0.27 | 0.30 |

The lowering of the Yellow Index in (2T) is effected without drastically affecting viscosity of the polyisocyanate.

EXAMPLE 3

This experiment describes a pair of extractions of the same crude polyisocyanate described in Example 1 above to form two different purified fractions (2Ta) and (2Tb) in accordance with the present process. This experiment shows the sensitivity of first to second solvent ratios in determining the final combination of color and viscosity in the purified fractions obtained. Only the purified fractions' properties are set forth in Table III for comparison with the Control properties. The residual fractions are not analyzed in this series.

The same procedure as described in Example 1 is employed except that the reagent bottle is 1-liter. The bottle is charged with 100 g (81 ml) of the polyisocyanate, 105.3 ml of methylene dichloride and 624 ml of pentane. After shaking and settling into two layers, a first top (1T) layer is separated and after solvent removal yields 54 g of polymethylene poly(phenyl isocyanate) or about 54 percent of the original polyisocyanate charge. This (1T) fraction is set aside. The bottom layer (1B) after solvent removal yields 47.1 g or about 47 percent of the original charge. The total of 101 percent is assumed to be residual solvent carry-over. This first extraction step is repeated twice again to obtain a supply of the (1B) fraction material.

In one second extraction a 62.2 g (50.4 ml) sample of the (1B) material with no remaining solvent is mixed with 130.1 ml of methylene dichloride and 319.9 ml of pentane in the reagent bottle, shaken vigorously as in Example 1 and allowed to stand for 3 hours to settle into two layers. The volume ratios in this step are 10/26/64 for the isocyanate/first solvent/second solvent. A second top layer (2T) is separated and stripped of solvent to provide 31.6 g of a purified fraction identified as (2Ta) with the properties set forth in Table III. It will be noted that this yield of (2Ta) represents about 51 percent of the charged (1B) fraction. The second bottom layer (2B) is set aside.

In another second extraction of the (1B) material, 60 g (48.6 ml) is extracted with 145.9 ml of methylene dichloride and 286.9 ml of pentane to provide another top and bottom layer. The volume ratios in this step are 10/30/60 for the isocyanate/first solvent/second solvent. The second top layer is separated and stripped of solvent to provide 38.3 g of a purified fraction identified as (2T*b*) with the properties set forth in Table III. This yield of (2T*b*) represents about 64 percent of the charged (1B) fraction. The second bottom layer is set aside.

Both purified fractions (2T*a*) and (2T*b*) are in accordance with the present invention having improved color and purity over the Control. However, the results show the effect that the first/second solvent ratios have on the properties of the purified fractions. As the ratio increases or pentane proportion decreases, more of the higher viscosity colored bodies remain in the top pentane layer as evidenced by 64 percent proportion of the (1B) charge in the (2T*b*) fraction. Conversely, the 51 percent carry-over in (2T*a*) is the result of the higher proportion of pentane forcing more of the higher viscosity colored bodies into the lower (2B) layer.

TABLE III

| Sample | Control | 2Ta | 2Tb |
|---|---|---|---|
| Viscosity (cps) at 25° C. | 191 | 194 | 451 |
| Yellow Index | 31.5 | 8.0 | 20.0 |
| Fe ppm | 6 | 0 | 0 |
| Isocyanate E.W. | 132.9 | 130.8 | 135.2 |

What is claimed is:

1. A process for extracting a crude organic polyisocyanate obtained from the phosgenation of a precursor organic polyamine to form a purified fraction and a residual fraction said process comprising:
   1. extracting said crude polyisocyanate in a first extractor with a solvent pair comprising at least one first solvent capable of solubilizing substantially all of said crude polyisocyanate and at least one second solvent capable of solubilizing all but the high boiling higher polymeric components present in said crude polyisocyanate thereby forming a first top layer comprising said second solvent and a first bottom layer comprising said first solvent;
   2. passing said first bottom layer, optionally through an evaporator, to a second extractor;
   3. extracting said first bottom layer in said second extractor with said solvent pair set forth above thereby forming a second top and second bottom layers;
   4. passing said second top layer through an evaporator to recover said second solvent as overhead and said purified fraction as residue; and
   5. passing said second bottom layer, optionally through an evaporator, and in combination with said first top layer to an evaporator to recover said second solvent, and, optionally, said first solvent as overhead and said residual fraction as residue.

2. A process according to claim 1 wherein said crude polyisocyanate comprises a polymethylene poly(phenyl isocyanate) mixture.

3. A process according to claim 1 wherein said crude polyisocyanate comprises a polymethylene poly(phenyl isocyanate) dissolved in the same or different first solvent employed in said first extracting step.

4. A process according to claim 1 wherein the proportions of said components in both said first and second extracting steps based on a total of 100 volume percent are from about 5 to about 20 volume percent polyisocyanate, from about 10 to about 35 volume percent first solvent, and from about 55 to about 85 volume percent second solvent.

5. A process according to claim 1 wherein the weight percent distribution of polyisocyanate material in each of said first and second top and bottom layers is from about 45 to about 55 percent by weight based on the input weight to each extracting step and wherein the total distribution is 100 percent.

6. A process according to claim 1 wherein said first solvent is selected from the group consisting of toluene, xylene, monochlorobenzene, dichlorobenzene, methylene dichloride, and mixtures thereof.

7. A process according to claim 1 wherein said first solvent is methylene dichloride.

8. A process according to claim 1 wherein said second solvent is an aliphatic hydrocarbon having from about 5 to about 10 carbon atoms.

9. A process according to claim 1 wherein said second solvent is pentane.

10. A process according to claim 1 wherein said second solvent is hexane.

11. A process according to claim 1 comprising the steps of continuously feeding to said first extractor a crude phosgene free polymethylene poly(phenyl isocyanate) feedstock obtained from the phosgenation of a polymethylene poly(phenyl amine) dissolved in the same or different first solvent employed in said first extracting step and wherein said solvent has been partially or fully stripped off, thereafter continuously carrying out the recited steps set forth in claim 1 to obtain said purified and residual fractions.

12. A process for extracting a crude mixture of polymethylene poly(phenyl isocyanate) to form a purified fraction and a residual fraction said process comprising:
   1. extracting in a first extractor in the proportions based on a total of 100 volume percent:
      (i) from about 5 to about 20 volume percent of said crude mixture of polymethylene poly(phenyl isocyanate);
      (ii) from about 10 to about 35 volume percent of a first solvent selected from the group consisting of toluene, xylene, monochlorobenzene, dichlorobenzene, methylene dichloride, and mixtures thereof; and
      (iii) from about 55 to about 85 volume percent of a second solvent comprising an aliphatic hydrocarbon having from about 5 to about 10 carbon atoms,
      thereby forming a first top layer comprising said second solvent and a first bottom layer comprising said first solvent;
   2. passing said first bottom layer to a second extractor;
   3. extracting said first bottom layer in said second extractor with the same first and second solvents falling within the same proportional ranges set forth above thereby forming second top and second bottom layers.
   4. passing said second top layer through an evaporator to recover said second solvent as overhead and said purified fraction as residue;
   5. passing said second bottom layer to an evaporator in combination with said first top layer to recover both first and second solvents as overhead and said residual fraction as residue.

13. A process according to claim 12 wherein said first solvent comprises methylene dichloride.

14. A process according to claim 13 wherein said second solvent comprises pentane.

15. A process according to claim 13 wherein said second solvent comprises hexane.

16. A process according to claim 12 wherein the distribution of polyisocyanate material in each of said first and second top and bottom layers is from about 45 to about 55 percent by weight based on input weight to each step and wherein the total distribution equals 100 percent.

* * * * *